(12) United States Patent
Komatsu (10) Patent No.: US 12,016,521 B2
(45) Date of Patent: Jun. 25, 2024

(54) ENDOSCOPE SYSTEM

(71) Applicant: HOYA CORPORATION, Tokyo (JP)

(72) Inventor: Masahiro Komatsu, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 90 days.

(21) Appl. No.: 17/799,174

(22) PCT Filed: Feb. 26, 2021

(86) PCT No.: PCT/JP2021/007247
§ 371 (c)(1),
(2) Date: Aug. 11, 2022

(87) PCT Pub. No.: WO2021/177148
PCT Pub. Date: Sep. 10, 2021

(65) Prior Publication Data
US 2023/0102158 A1    Mar. 30, 2023

(30) Foreign Application Priority Data

Mar. 3, 2020 (JP) .................................. 2020-035625

(51) Int. Cl.
*H04N 23/50* (2023.01)
*A61B 1/00* (2006.01)
(Continued)

(52) U.S. Cl.
CPC .... *A61B 1/000095* (2022.02); *A61B 1/00124* (2013.01); *H04N 5/265* (2013.01);
(Continued)

(58) Field of Classification Search
CPC .......... A61B 1/00018; A61B 1/000095; A61B 1/00124; H04N 23/555
See application file for complete search history.

(56) References Cited

U.S. PATENT DOCUMENTS 8,279,769 B2 * 10/2012 den Besten ......... G06F 13/4072
370/252
9,247,867 B2 * 2/2016 Baum .................. A61B 1/0653
(Continued)

FOREIGN PATENT DOCUMENTS

JP    6-327623 A    11/1994
JP    2012-115531 A    6/2012
(Continued)

OTHER PUBLICATIONS

International Search Report (ISR) dated Apr. 27, 2021 filed in PCT/JP2021/007247.
(Continued)

*Primary Examiner* — Brian P Yenke
(74) *Attorney, Agent, or Firm* — GREENBLUM & BERNSTEIN, P.L.C.

(57) ABSTRACT

Proposed is a technology that enables a video signal (endoscopic image) output from an imaging unit to be processed without signal conversion according to an MIPI D-PHY standard. The present disclosure proposes an endoscope system including: an endoscope device that includes an endoscope-side connector unit; a processor that includes a processor-side connector unit; and an attenuation correction unit that corrects attenuation of a video signal from an image sensor disposed at a distal end portion of the endoscope device (FIG. 3).

8 Claims, 9 Drawing Sheets

(51) Int. Cl.
    *H04N 5/265*         (2006.01)
    *H04N 7/015*         (2006.01)
    *H04N 23/667*       (2023.01)

(52) U.S. Cl.
    CPC ........... *H04N 7/015* (2013.01); *H04N 23/555* (2023.01); *H04N 23/667* (2023.01)

(56) References Cited

U.S. PATENT DOCUMENTS

| | | | |
|---|---|---|---|
| 9,491,495 B2 * | 11/2016 | Bohm | H04L 25/4904 |
| 9,876,974 B2 * | 1/2018 | Okawa | H04N 7/183 |
| 10,668,888 B2 * | 6/2020 | Moon | B60R 21/233 |
| 10,902,572 B1 * | 1/2021 | Kennedy | G06T 5/90 |
| 10,973,394 B2 * | 4/2021 | Ogata | A61B 1/0676 |
| 11,023,409 B2 * | 6/2021 | Ahmed | G06F 13/4295 |
| 11,394,911 B2 * | 7/2022 | Osawa | A61B 1/00006 |
| 2008/0262299 A1 * | 10/2008 | Niida | A61B 1/05 600/110 |
| 2012/0016202 A1 | 1/2012 | Baum et al. | |
| 2012/0310045 A1 * | 12/2012 | Hu | A61B 1/00018 600/110 |
| 2013/0012777 A1 | 1/2013 | Baum et al. | |
| 2013/0225067 A1 | 8/2013 | Card et al. | |
| 2015/0138328 A1 * | 5/2015 | Yokohama | A61B 1/045 348/65 |
| 2016/0345812 A1 * | 12/2016 | Ogasawara | H04N 23/56 |
| 2016/0374538 A1 * | 12/2016 | Tanabe | A61B 1/05 600/132 |
| 2016/0381278 A1 * | 12/2016 | Kang | H04N 5/265 348/68 |
| 2017/0184837 A1 * | 6/2017 | Kang | A61B 1/00013 |
| 2018/0289247 A1 | 10/2018 | Koshika | |
| 2018/0296065 A1 | 10/2018 | Ono et al. | |
| 2019/0046022 A1 * | 2/2019 | Matsui | G02B 23/26 |
| 2019/0116332 A1 * | 4/2019 | Adachi | G02B 23/2484 |
| 2019/0373197 A1 * | 12/2019 | Harada | A61B 1/05 |
| 2020/0060532 A1 * | 2/2020 | Kang | A61B 1/045 |
| 2021/0185254 A1 * | 6/2021 | Osawa | A61B 1/018 |
| 2022/0311911 A1 * | 9/2022 | Kobayashi | H04N 23/555 |
| 2023/0190081 A1 * | 6/2023 | Schwarz | A61B 1/00183 600/109 |
| 2023/0319252 A1 * | 10/2023 | K | G06F 13/4282 348/42 |

FOREIGN PATENT DOCUMENTS

| | | |
|---|---|---|
| JP | 5861071 B1 | 2/2016 |
| JP | 2019-37789 A | 3/2019 |
| WO | 2017/104190 A1 | 6/2017 |
| WO | 2017/122586 A1 | 7/2017 |

OTHER PUBLICATIONS

European Search report dated Mar. 7, 2024, issued in EPO application No. 21763646.3.

Lee, Pil-Ho et al., "A 20—*GB/s Receiver Bridge Chip With Auto—Skew Calibration for MIPI D—PHY Interface*", IEEE Transactions on Consumer Electronics, IEEE Service Center, New York, NY, US, vol. 65, No. 4, Nov. 1, 2019 (Nov. 1, 2019), pp. 484-492, XP011751600, ISSN: 0098-3063, DOI: 10.1109/TCE.2019.2942503.

Notice of Reasons for Refusal dated Feb. 20, 2024, issued in Japanese application No. 2020-035625, together with an English translation.

* cited by examiner

ENDOSCOPE SYSTEM

TECHNICAL FIELD

The present disclosure relates to an endoscope system.

BACKGROUND ART

In general, an endoscope system includes an endoscope device (scope) and a processor that connects the endoscope device. In recent years, for example, attempts have been made to transmit an endoscopic image captured using an imaging unit (image sensor) conforming to a signal transmission standard called MIPI D-PHY to the processor.

However, since the MIPI D-PHY is a standard determined considering a transmission distance of several tens of centimeters, it does not guarantee a long transmission distance from the imaging unit to the processor via an insertion portion of the endoscope. Therefore, for example, as disclosed in Patent Literature 1, a technology has been developed in which a relay board for converting an MIPI D-PHY signal into a signal having a higher speed than that of the MIPI D-PHY signal is disposed in an insertion portion or an operation unit of an endoscope device, and a signal can be transmitted over a long distance to a processor.

CITATION LIST

Patent Literature

Patent Literature 1: JP 5861071 B2

SUMMARY OF INVENTION

Technical Problem

However, since the insertion portion of the endoscope device is bent, it is desirable to avoid disposing the relay board also in terms of space. In addition, since various channels and the like are arranged in the operation unit, it is also structurally difficult to dispose the relay board in the operation unit.

Considering such a constraint, it is desirable to transmit a signal according to the MIPI D-PHY as it is so that the signal can be processed by the processor. In this regard, as described above, in a case where a signal according to the MIPI D-PHY is transmitted as it is, the signal is attenuated by transmission over a long distance, and the processor cannot appropriately process the endoscopic image.

In view of such a situation, the present disclosure proposes a technology that enables a video signal (endoscopic image) output from an imaging unit to be processed without signal conversion according to an MIPI D-PHY standard.

Solution to Problem

In order to solve the above problem, the present embodiment proposes an endoscope system including an endoscope device that includes an endoscope-side connector unit, a processor that includes a processor-side connector unit, and an attenuation correction unit that corrects attenuation of a video signal from an image sensor disposed at a distal end portion of the endoscope device.

Further features related to the present disclosure will become apparent from the description of the present specification and the accompanying drawings. The present disclosure is achieved and implemented by elements and combinations of various elements and by modes of the following detailed description and the appended claims.

It is to be understood that the description in this specification is merely exemplary and is not intended to limit the significance of the claims or the application in any way.

Advantageous Effects of Invention

According to the present disclosure, it is possible to process a video signal (endoscopic image) output from the imaging unit without signal conversion according to the MIPI D-PHY standard.

BRIEF DESCRIPTION OF DRAWINGS

FIG. 4A illustrates an example of an output signal (MIPI D-PHY signal: video signal) of an imaging unit 103. FIG. 4B illustrates an example of a signal (before separation) that is transmitted through a signal cable and input to the scope connector circuit 401. FIG. 4C illustrates an example of a signal (LP mode signal) after separation. FIG. 4D illustrates an example of a signal (HS mode signal) after separation and equalizer processing.

DESCRIPTION OF EMBODIMENTS

Hereinafter, embodiments of the present disclosure will be described with reference to the drawings. In the following, an endoscope system will be described as an embodiment of the present disclosure.

An observation target site in the endoscope system is, for example, respiratory organs or digestive organs. Examples of the respiratory organs include the lungs, the bronchus, the ears, the nose, and the throat. Examples of the digestive organs include the large intestine, the small intestine, the stomach, the esophagus, the duodenum, the uterus, and the bladder. In a case of observing the target sites as described above, it is more effective to utilize an image in which a specific biological structure is emphasized.

<Configuration of Endoscope System>

Figure 1:
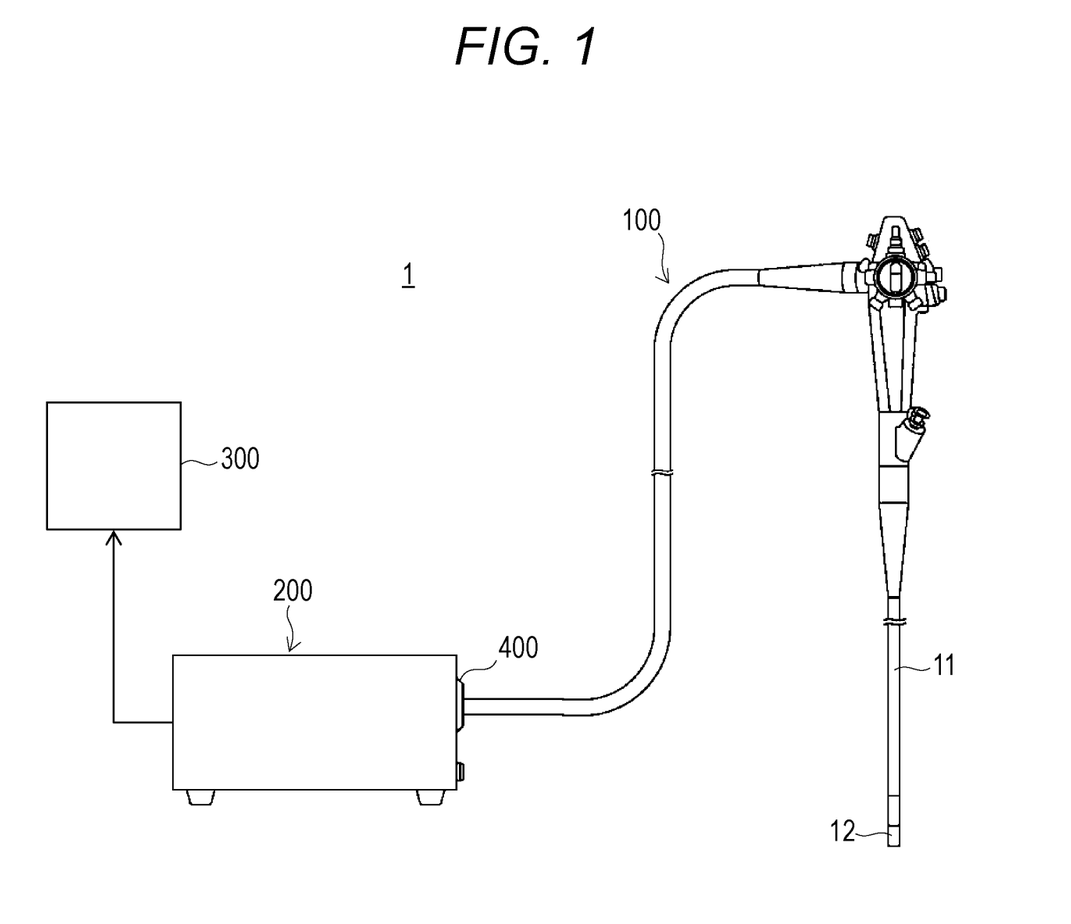
FIG. 1 is a diagram illustrating an overall external configuration example of an endoscope system according to the present embodiment.
Figure 2:
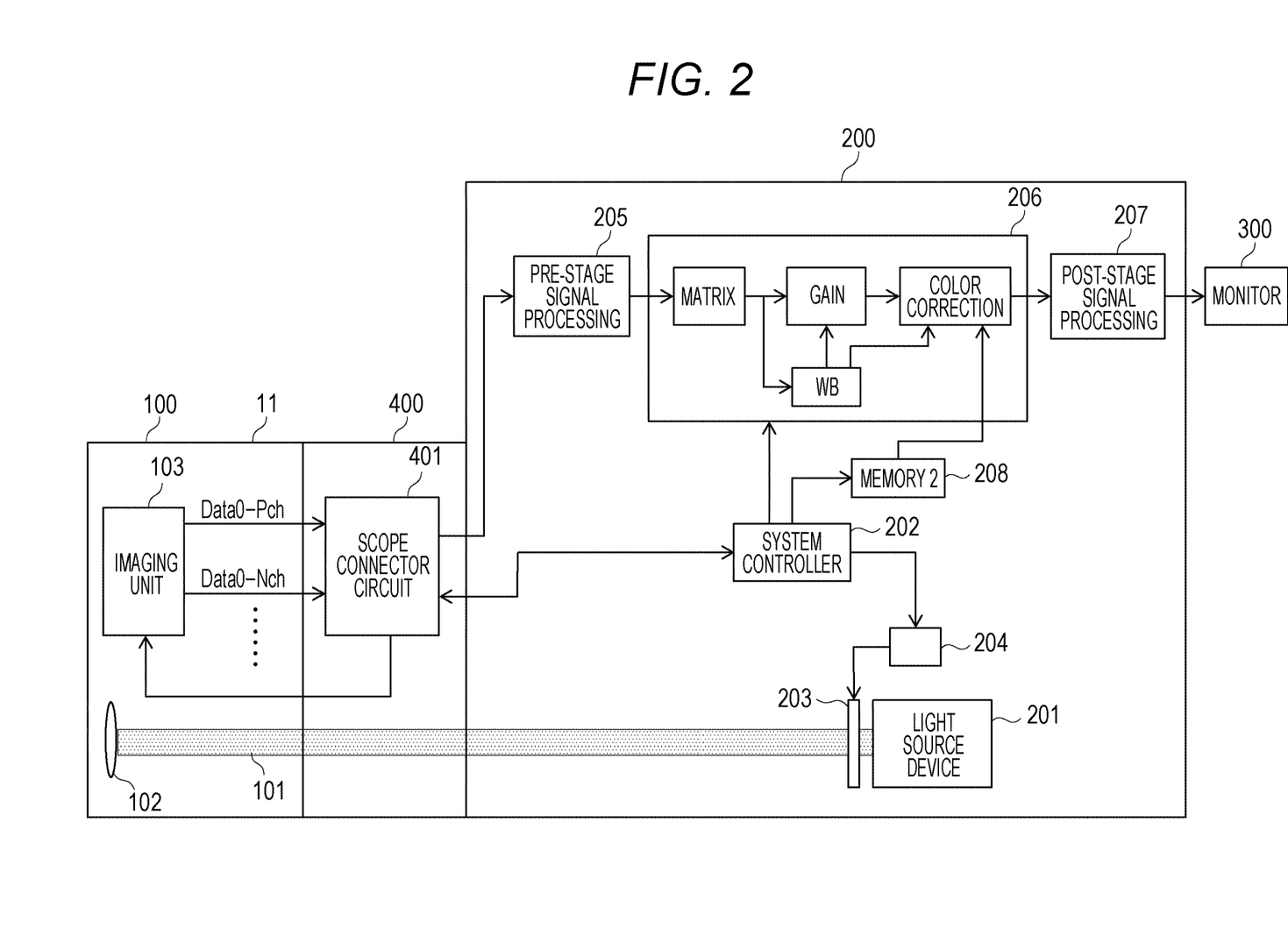
FIG. 2 is a diagram illustrating a schematic internal configuration example of the endoscope system according to the present embodiment.

FIG. 1 is a diagram illustrating an example of an overall appearance of an endoscope system of the present embodiment, and FIG. 2 is a diagram illustrating a schematic internal configuration example of the endoscope system of the present embodiment. An endoscope system 1 includes an endoscope device (electronic scope) 100, a processor 200, and a monitor 300. Note that a scope connector (which may hereinafter be simply referred to as a "connector") 400 including a connector circuit according to a feature of the present embodiment is provided at a processor-side end portion of the endoscope device 100.

The endoscope device 100 includes an elongated tubular insertion portion 11 configured to be inserted into a subject. The endoscope device 100 includes a light carrying bundle (LCB) 101 for guiding irradiation light from a light source device 201 to be described later, a light distribution lens 102 provided at an emission end of the LCB 101, an imaging unit 103 that receives return light from an irradiated portion (observation site) via an objective lens (not illustrated), a driver signal processing circuit 105 that drives the imaging unit 103, and a first memory 106.

The irradiation light from the light source device 201 enters the LCB 101 and propagates by repeating total reflection in the LCB 101. The irradiation light propagating in the LCB 101 is emitted from the emission end of the LCB 101 disposed in a distal end portion 12 of the insertion portion 11, and irradiates the observation site through the light distribution lens 102. The return light from the irradiated portion forms an optical image by each pixel on a light receiving surface of the imaging unit 103 via the objective lens.

The imaging unit 103 is disposed in the distal end portion 12 of the insertion portion 11 and is, for example, a charge coupled device (CCD) image sensor. The imaging unit 103 accumulates an optical image (return light from a living tissue) formed by each pixel on the light receiving surface, as charges corresponding to the amount of light, and generates and outputs image signals of R, G, and B. Note that the imaging unit 103 is not limited to a CCD image sensor, and may be replaced with a Complementary Metal Oxide Semiconductor (CMOS) image sensor or other types of imaging devices. A signal output from the imaging unit 103 is processed by a scope connector circuit 401 provided in the scope connector 400 as described later.

The processor 200 is a device that integrally includes a signal processing device that processes a signal from the endoscope device 100 and a light source device that irradiates, via the endoscope device 100, a body cavity having difficulty in receiving natural light. In another embodiment, the signal processing device and the light source device may be provided separately. The processor 200 includes the light source device 201, a system controller 202, an optical filter 203, an optical filter driver 204, a pre-stage signal processing circuit 205, a color conversion circuit 206, a post-stage signal processing circuit 207, and a second memory 208.

The processor 200 may include an operation panel (not illustrated). The operation panel may have various configurations. Examples of a specific configuration of the operation panel include a hardware key for each function mounted on a front surface of the processor 200, a touch panel type graphical user interface (GUI), a combination of a hardware key and a GUI, and the like. An operator can perform a mode switching operation described later with the operation panel.

The system controller 202 executes various programs stored in a memory (not illustrated) and integrally controls the entire endoscope system 1. The system controller 202 controls the operations and timings of various circuits in the processor 200 by using a control signal so as to perform processing suitable for the endoscope device 100 connected to the processor 200. Further, the system controller 202 may be connected to the above-described operation panel. The system controller 202 changes each operation of the endoscope system 1 and a parameter for each operation in accordance with an operator's instruction input to the operation panel.

As the light source device 201, for example, a high-brightness lamp such as a xenon lamp, a halogen lamp, a mercury lamp, or a metal halide lamp, or a light emitting diode (LED) can be used. The irradiation light from the light source device 201 is light having a spectrum mainly spreading from a visible light range to an invisible infrared range (or light including at least the visible light range). The irradiation light from the light source device 201 is incident on the optical filter 203.

Data communication between the endoscope device 100 and the processor 200 may use a wired electric communication scheme or an optical wireless communication scheme.

As illustrated in FIG. 2, the endoscope device 100 and the processor 200 are connected via the scope connector 400. The connector 400 includes an LCB constituting a part of the LCB 101 continuing from the processor 200 to the endoscope device 100, and the scope connector circuit 401. The scope connector circuit 401 separates a low power (LP) mode signal and a high speed (HS) mode signal included in a MIPI D-PHY signal (video signal) output from the imaging unit 103, corrects (amplification by an equalizer and sensor-specific noise correction) the video signal attenuated by cable transmission in the endoscope device 100, multiplexes again the LP mode signal and the corrected HS mode signal, and supplies the multiplexed signal to the processor 200, which will be described in detail later. Further, the scope connector circuit 401 is provided in the scope connector 400 in the present embodiment, but is not necessarily provided in the scope connector 400. For example, a circuit corresponding to the scope connector circuit 401 may be provided in a connector unit on the processor 200 side or inside the processor 200.

<Internal Configuration Example of Scope Connector Circuit 401>

Figure 3:
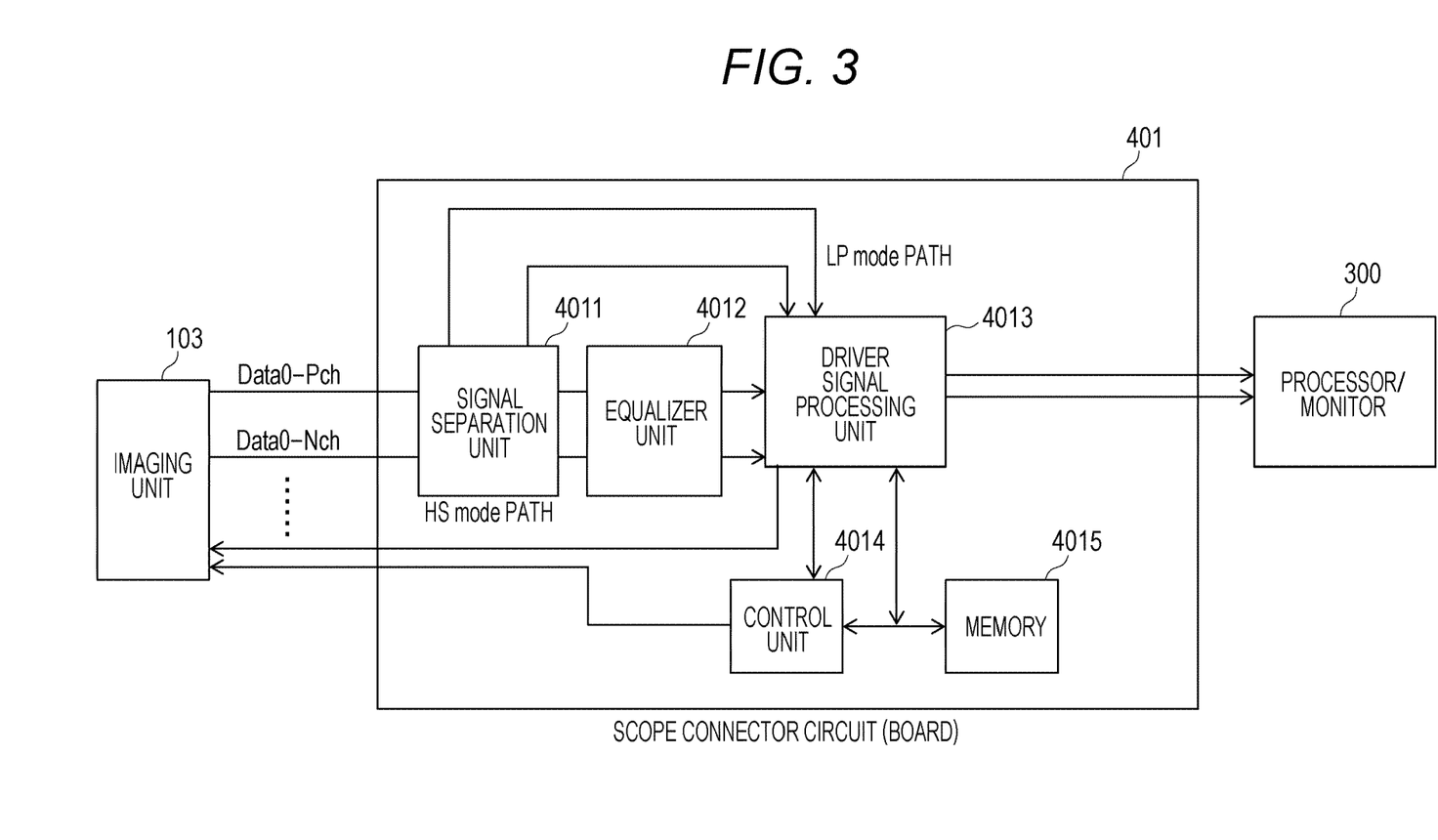
FIG. 3 is a diagram illustrating an internal configuration example of a scope connector circuit 401 included in a scope connector 400.
Figure 4:
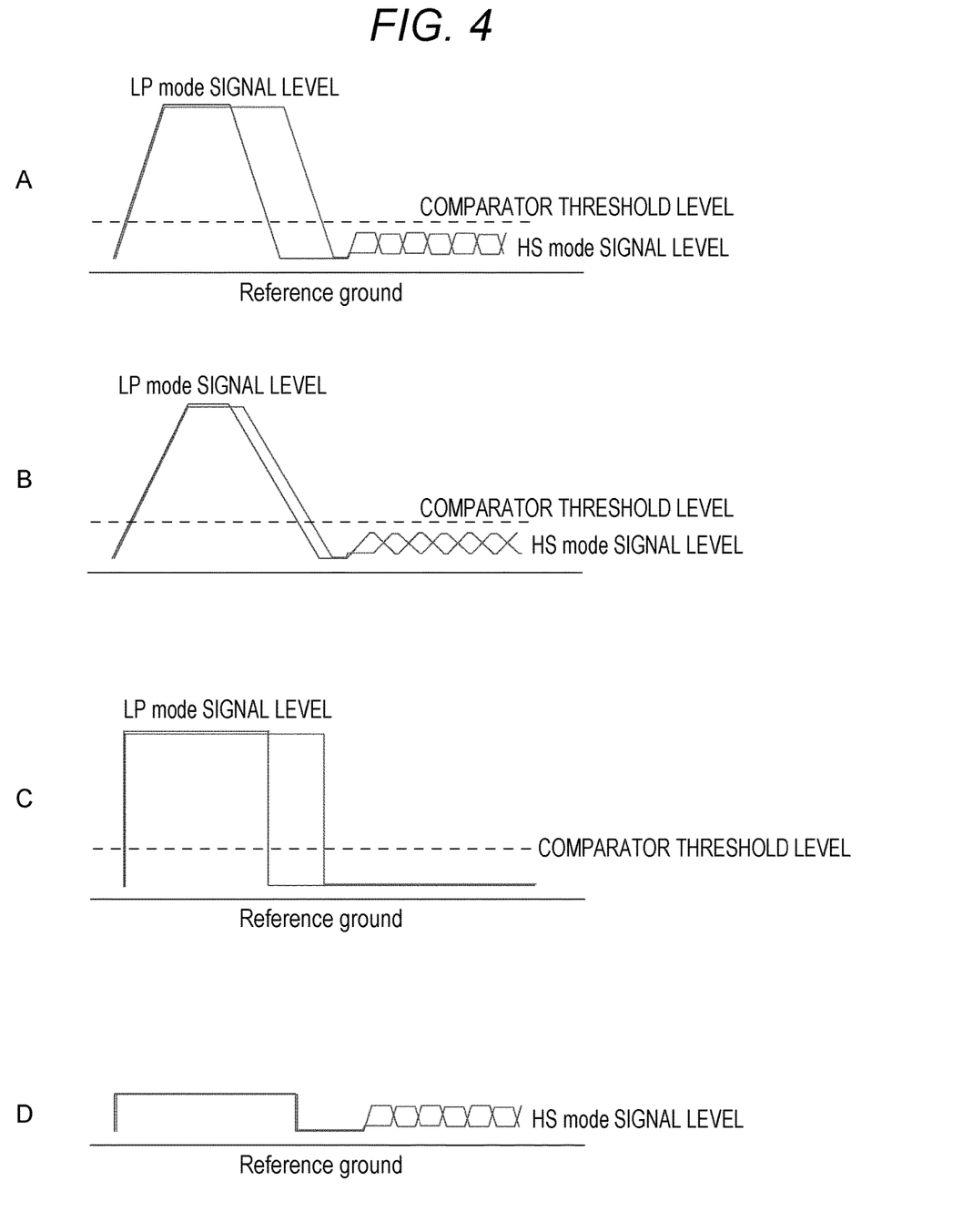
FIG. 4 is a diagram illustrating an example of a signal handled by the scope connector circuit 401.

FIG. 3 is a diagram illustrating an internal configuration example of the scope connector circuit 401 included in the scope connector 400. FIG. 4 is a diagram illustrating an example of a signal handled by the scope connector circuit 401. FIG. 4A illustrates an example of an output signal (MIPI D-PHY signal: video signal) of the imaging unit 103. FIG. 4B illustrates an example of a signal (before separation) that is transmitted through a signal cable and input to the scope connector circuit 401. FIG. 4C illustrates an example of a signal (LP mode signal) after separation. FIG. 4D illustrates an example of a signal (HS mode signal) after separation and equalizer processing.

The scope connector circuit 401 includes a signal separation unit 4011 that separates the MIPI D-PHY signal output from the imaging unit 103 and transmitted through the signal cable into the LP mode signal and the HS mode signal, an equalizer unit 4012 that amplifies the HS mode signal obtained by the separation to correct a distorted gain, a driver signal processing unit 4013 that is implemented by, for example, an FPGA and corrects noise (point damage) unique to the imaging unit 103 or multiplexes the LP mode signal and the corrected HS mode signal and outputs the multiplexed signal to the processor 200, a control unit 4014 that performs register setting or the like (for example, setting for changing a shutter speed and a gain according to brightness and darkness in the body into which the scope is inserted) of the imaging unit 103, and a memory 4015 that stores an initial setting value of the imaging unit 103, configuration data of the driver signal processing unit 4013, and the like. Note that the number of video lanes (the number of chs) from the imaging unit 103 is determined by the resolution of the image sensor. Further, the driver signal processing unit 4013 may be caused to perform the processing performed by the control unit 4014.

The signal (MIPI D-PHY signal) output from the imaging unit 103 is, for example, a signal in a form in which the high speed mode (HS mode) signal is transmitted after the low power mode (LP mode) signal is transmitted. As illustrated in FIG. 4A, the low power mode (LP mode) signal has a higher larger level (voltage amplitude) and a lower transmission rate than the high speed mode (HS mode) signal. Since the transmission rate is low, it can be said that degradation of the signal level of the low power mode (LP mode) signal due to cable transmission is less likely to occur than the high speed mode (HS mode) signal.

In a case where the MIPI D-PHY signal is transmitted through the signal cable of the endoscope device 100 (over a distance longer than a distance recommended by the MIPI D-PHY standard), the low power mode (LP mode) signal and the high speed mode (HS mode) signal are distorted as illustrated in FIG. 4B. The signal level of the low power mode (LP mode) signal is higher than a comparator threshold level (a threshold for distinguishing and extracting the LP mode signal) even if the signal is somewhat blurred, and thus it can be seen that the low power mode (LP mode) signal is hardly affected by cable transmission. On the other hand, since the signal level of the high speed mode (HS mode) signal itself is low, the signal is distorted by cable transmission, and it is difficult for the processor at the subsequent stage to perform signal processing as it is. Therefore, in the present embodiment, the equalizer unit 4012 amplifies the distorted high speed mode (HS mode) signal to perform level correction so as not to affect signal processing in the subsequent stage.

The low power mode (LP mode) signal obtained by being separated by the signal separation unit 4011 can be extracted as a clean square wave as illustrated in FIG. 4C by setting an appropriate comparator threshold level even if the signal is somewhat distorted by cable transmission (FIG. 4B).

As illustrated in FIG. 4D, the level of the high speed mode (HS mode) signal separated by the signal separation unit 4011 and corrected by the equalizer unit 4012 is corrected to implement a clear differential signal like the HS mode signal portion of the MIPI D-PHY signal (FIG. 4A) before separation.

<Internal Configuration Example of Signal Separation Unit 4011>

FIGS. 5 to 9 are diagrams related to an internal configuration example of the signal separation unit 4011.

(i) Configuration Example 1

Figure 5:
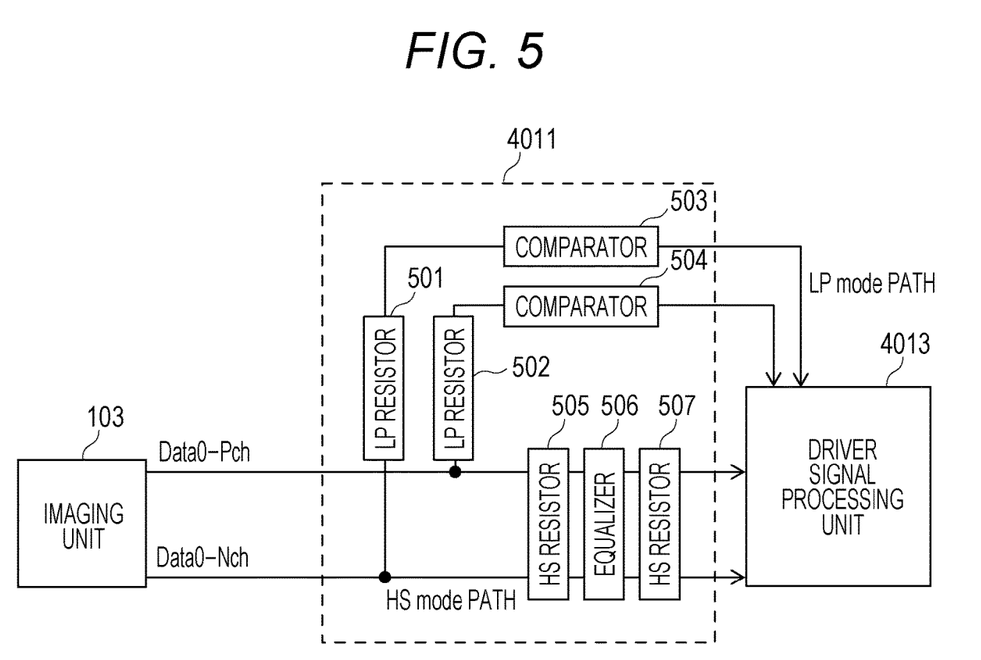
FIG. 5 is a diagram illustrating an internal configuration example 1 of a signal separation unit 4011.

The signal separation unit 4011 according to the internal configuration example illustrated in FIG. 5 includes a plurality of LP resistors 501 and 502 connected in series with video chs (Data0-Pch, Data0-Nch, . . . , DataN-Pch, and DataN-Nch), a plurality of comparators 503 and 504 that extract (a value of a signal whose level is higher than the threshold level is 1, and a value of a signal whose level is lower than the threshold level is 0) and output a signal whose level is higher than a predetermined comparator threshold level, a plurality of HS resistors 505 and 507 connected in parallel with the video chs, and an equalizer 506 that is connected in parallel with the video chs between the HS resistors 505 and 507, cuts off the low power mode (LP mode) signal, and corrects (amplifies) the high speed mode (HS mode) signal attenuated by cable transmission.

Resistance values of the LP resistors 501 and 502 are larger than resistance values of the HS resistors 505 and 507, and can be, for example, 100Ω or more. It is possible to prevent deterioration in signal quality at the time of transmitting the HS mode signal by making the impedance of an LP mode path higher than that of an HS mode path. In addition, although the HS resistors 505 and 507 are not essential components, the impedance on an input side of the equalizer 506 and the impedance on an output side (an input side of the driver signal processing unit (for example, FPGA) 4013) can be matched by arranging the HS resistors 505 and 507.

The comparator threshold of the comparators 503 and 504 can be arbitrarily (in advance) determined based on the voltage amplitude of HS mode. For example, the comparator threshold can be 220 mV, 385 mV, or 550 mV. A signal whose level is equal to or higher than the comparator threshold is extracted as the LP mode signal, and a pulse signal as illustrated in FIG. 4C is supplied to the driver signal processing unit 4013.

(ii) Configuration Example 2

Figure 6:
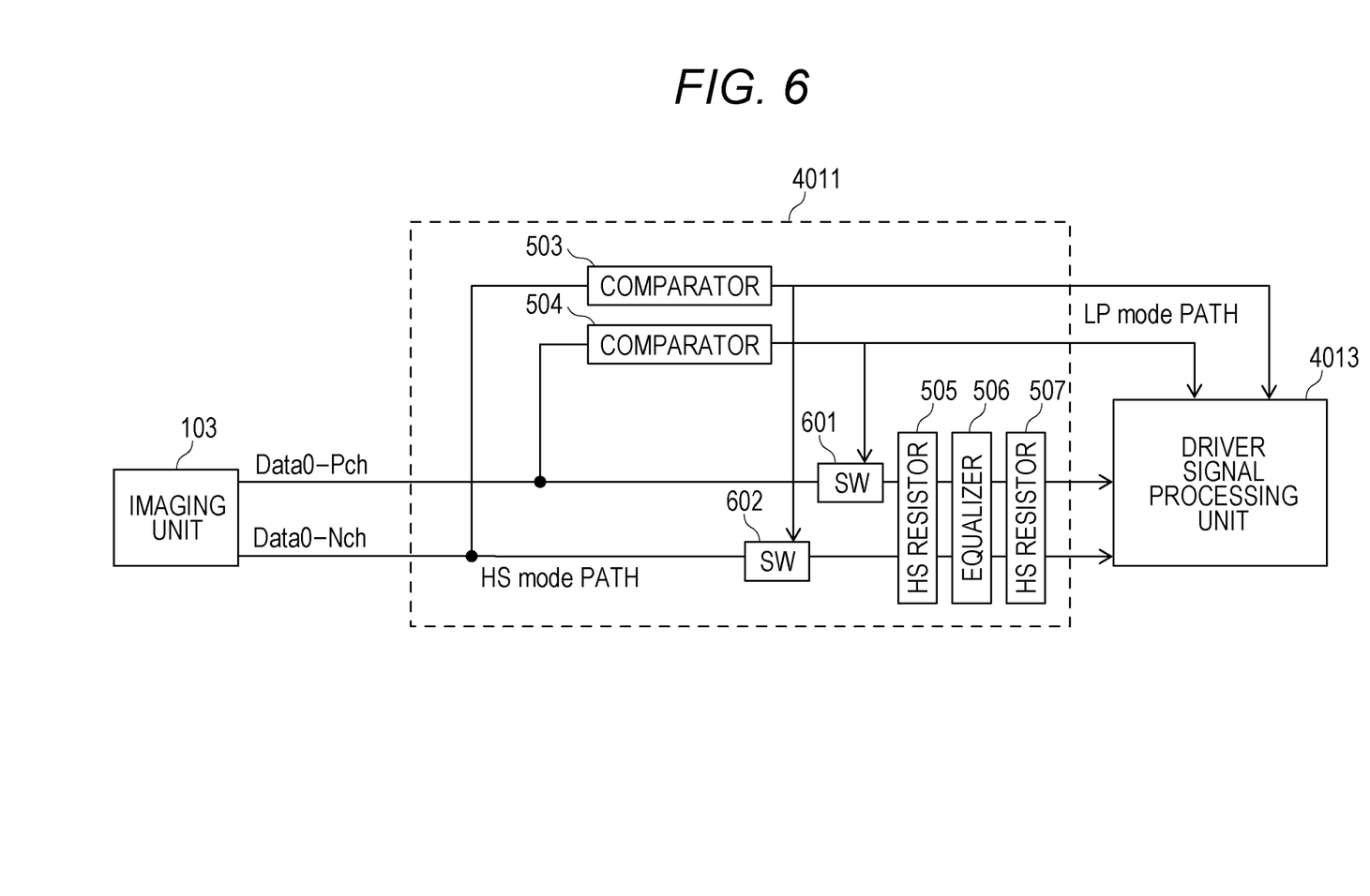
FIG. 6 is a diagram illustrating an internal configuration example 2 of the signal separation unit 4011.

The signal separation unit 4011 according to the internal configuration example illustrated in FIG. 6 includes a plurality of comparators 503 and 504 that are connected in series with video chs (Data0-Pch, Data0-Nch, . . . , DataN-Pch, and DataN-Nch), extract (a value of a signal whose level is higher than the threshold level is 1, and a value of a signal whose level is lower than the threshold level is 0) and output a signal whose level is higher than a predetermined comparator threshold level, a plurality of switches 601 and 602 that are connected in series with the video chs and operated by outputs of the comparators 503 and 504, a plurality of HS resistors 505 and 507 connected in parallel with the switches 601 and 602, and an equalizer 506 that is connected in parallel with the video chs between the HS resistors 505 and 507 and corrects (amplifies) the high speed mode (HS mode) signal attenuated by cable transmission.

The switches 601 and 602 are controlled to be turned on at a falling timing of the LP mode signal in FIG. 4C after the extraction of the LP mode signal is completed by the comparators 503 and 504. Once the switches 601 and 602 are turned on, a signal (a portion corresponding to the HS mode signal in FIG. 4B) is supplied to the equalizer, and attenuation is corrected (amplified).

Note that the comparator threshold and the HS resistors 505 and 507 are as described in the configuration example 1.

(iii) Configuration Example 3

Figure 7:
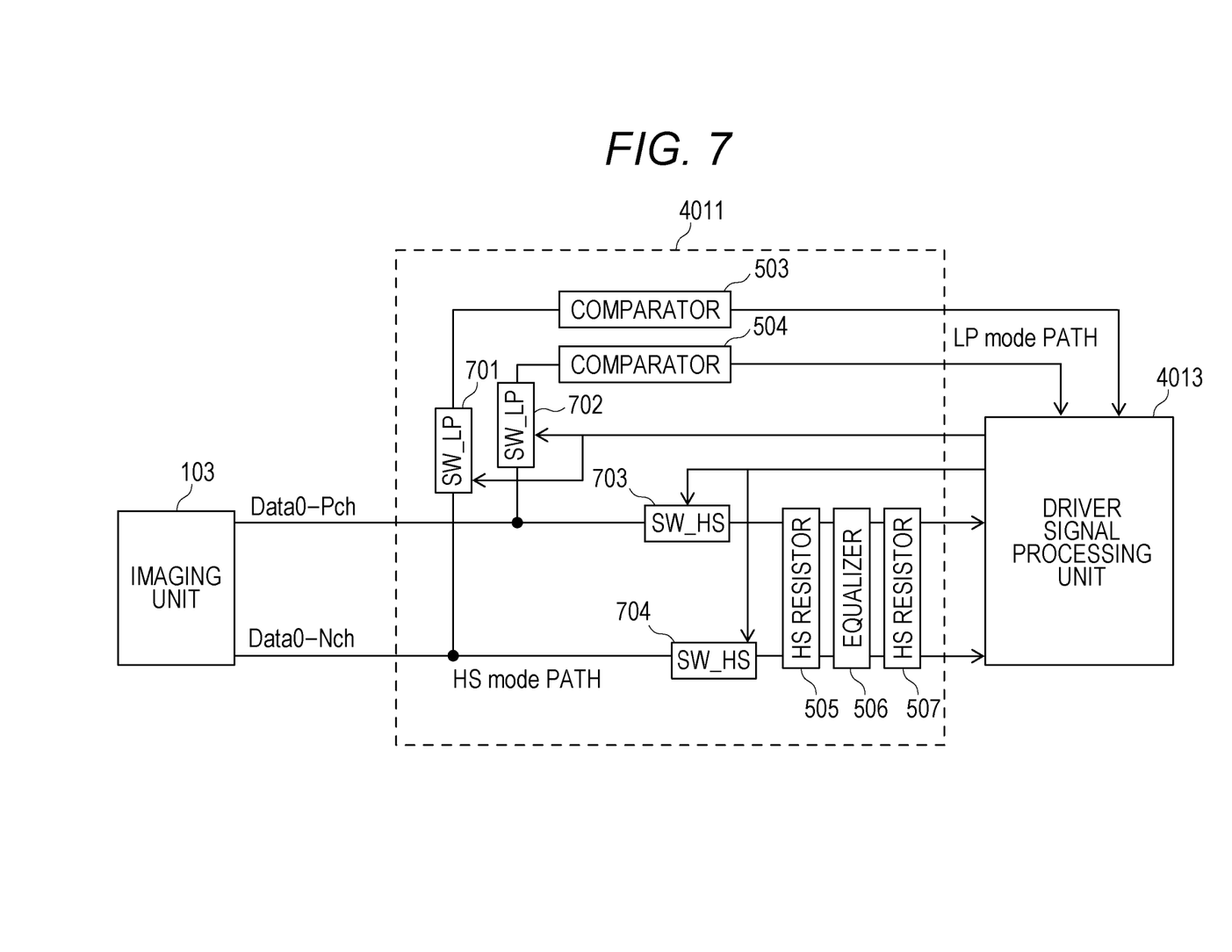
FIG. 7 is a diagram illustrating an internal configuration example 3 of the signal separation unit 4011.

The signal separation unit 4011 according to the internal configuration example illustrated in FIG. 7 includes a plurality of LP mode switches (SW_LPs) 701 and 702 connected in series with video chs (Data0-Pch, Data0-Nch, . . . , DataN-Pch, and DataN-Nch), a plurality of comparators 503 and 504 that extract (a value of a signal whose level is higher than the threshold level is 1, and a value of a signal whose level is lower than the threshold level is 0) and output a signal whose level is higher than a predetermined comparator threshold level, HS mode switches (SW_HSs) 703 and 704 connected in series with the video chs, a plurality of HS resistors 505 and 507 connected in parallel with the SW_HSs 703 and 704, and an equalizer 506 that is connected in parallel with the video chs between the HS resistors 505 and 507 and corrects (amplifies) the high speed mode (HS mode) signal attenuated by cable transmission.

The driver signal processing unit 4013 (or a control unit (not illustrated) such as a separately provided central processing unit (CPU)) controls the SW_LPs 701 and 702 to be turned on and controls the SW_HSs 703 and 704 to be turned off so as to supply all the received video signals (MIPI D-PHY signals) to the LP mode path side at a first timing (initial operation period) at which the video signals are received from the imaging unit 103. Then, the driver signal processing unit 4013 acquires an appearance timing (appearance position) of the LP mode signal from the video signals acquired in the initial operation period. Since the period of one cycle of the video signal (MIPI D-PHY signal) is known in advance, in an operation period after the initial operation period, the driver signal processing unit 4013 controls the SW_LPs 701 and 702 to be turned on and controls the SW_HSs 703 and 704 to be turned off in a period in which the LP mode signal arrives, and controls the SW_LPs 701 and 702 to be turned off and controls the SW_HSs 703 and 704 to be turned on in a period in which the HS mode signal arrives.

The LP mode signal of the LP mode path acquired by the switching operation is shaped by the comparators 503 and 504 and supplied to the driver signal processing unit 4013. On the other hand, the attenuation of the HS mode signal of the HS mode path acquired by the switching operation is corrected by the equalizer 506 and supplied to the driver signal processing unit 4013.

Note that the comparator threshold and the HS resistors 505 and 507 are as described in the configuration example 1.

(iv) Configuration Example 4

Figure 8:
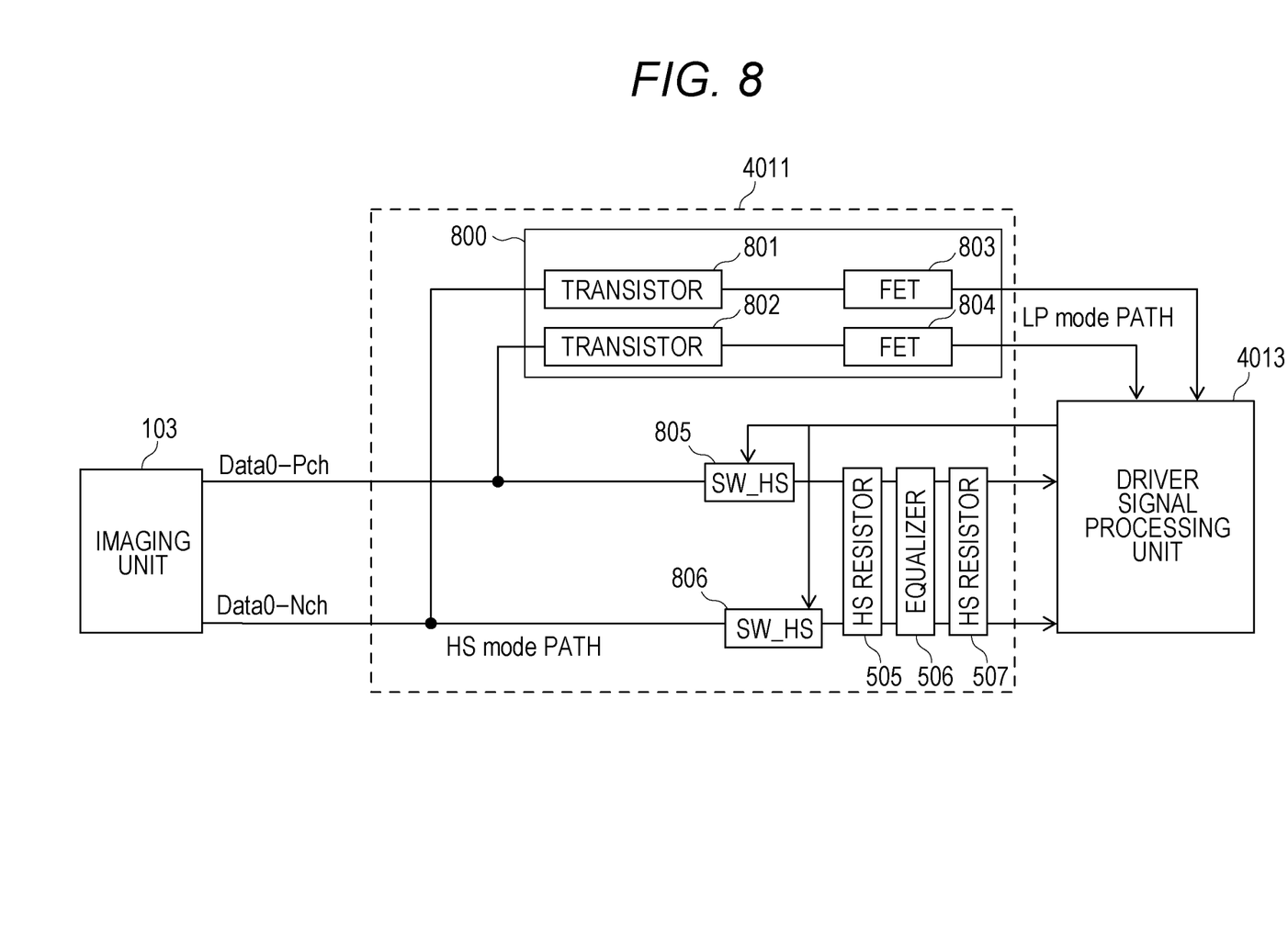
FIG. 8 is a diagram illustrating an internal configuration example 4 of the signal separation unit 4011.

The signal separation unit 4011 according to the internal configuration example illustrated in FIG. 8 includes transistors 801 and 802 (transistors are used instead of the LP mode switches (SW_LPs) 701 and 702 of the configuration example 3 (FIG. 7)) connected in series with video chs (Data0-Pch, Data0-Nch, . . . , DataN-Pch, and DataN-Nch), field effect transistors (FETs) 803 and 804 (FETs are used instead of the comparators 503 and 504) connected in series with the transistors 801 and 802, respectively, HS mode switches (SW_HSs) 805 and 806 connected in series with the video chs, a plurality of HS resistors 505 and 507 connected in parallel with the SW_HSs 805 and 806, and an equalizer 506 that is connected in parallel with the video chs between the HS resistors 505 and 507, and corrects (amplifies) the high speed mode (HS mode) signal attenuated by cable transmission.

The driver signal processing unit 4013 (or a control unit (not illustrated) such as a separately provided CPU) controls the SW_HSs 805 and 806 to be turned off so as to supply all the received video signals (MIPI D-PHY signals) to the LP mode path side at a first timing (initial operation period) at which the video signals are received from the imaging unit 103. Then, the driver signal processing unit 4013 acquires an appearance timing (appearance position) of the LP mode signal from the video signals acquired in the initial operation period. Since the period of one cycle of the video signal (MIPI D-PHY signal) is known in advance, in an operation period after the initial operation period, the driver signal processing unit 4013 controls the SW_HSs 805 and 806 to be turned off in a period in which the LP mode signal arrives, and controls the SW_HSs 805 and 806 to be turned on in a period in which the HS mode signal arrives.

The LP mode signal of the LP mode path acquired by the switching operation is shaped by the FETs 803 and 804 and supplied to the driver signal processing unit 4013. On the other hand, the attenuation of the HS mode signal of the HS mode path acquired by the switching operation is corrected by the equalizer 506 and supplied to the driver signal processing unit 4013.

Note that the comparator threshold and the HS resistors 505 and 507 are as described in the configuration example 1.

Figure 9:
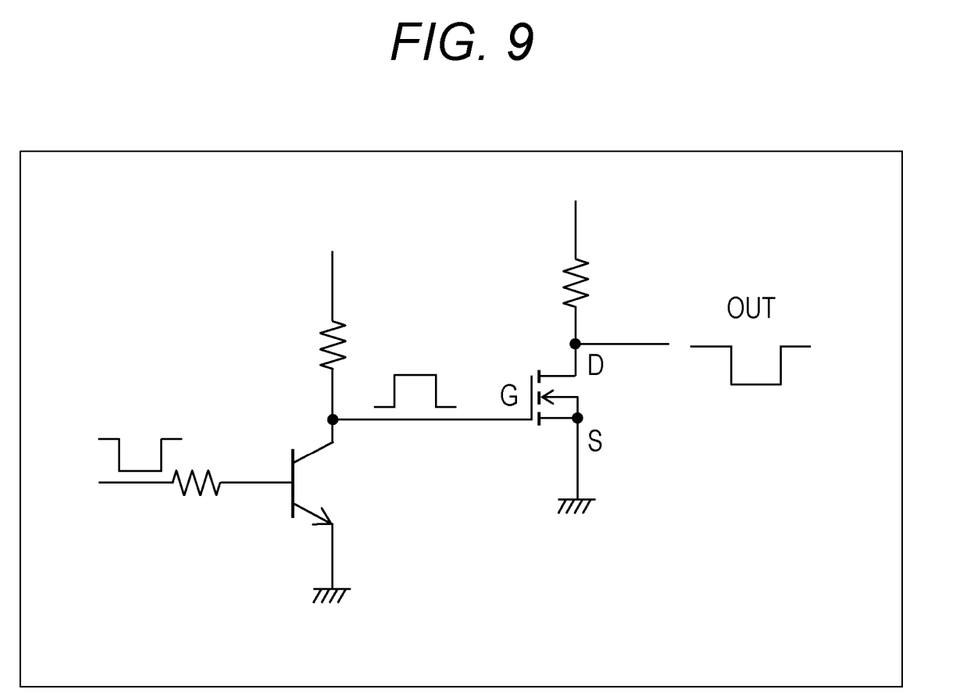
FIG. 9 is a diagram illustrating detailed configurations of transistors 801 and 802 and field effect transistors (FETs) 803 and 804 in the internal configuration example 4 of the signal separation unit 4011.

FIG. 9 is a diagram illustrating detailed configurations of the transistors 801 and 802 and the FETs 803 and 804 in the configuration example 4. The LP mode signal (pulse) can be extracted by combining the transistors 801 and 802 and the FETs 803 and 804.

<Effects of Present Embodiment>

According to the present embodiment, the scope connector circuit 401 is provided in the scope connector 400 of the endoscope device 100, and a video signal (a signal based on the MIPI D-PHY standard) from the imaging unit (image sensor) 103 is subjected to signal processing. Specifically, the scope connector circuit (attenuation correction unit) 401 separates the LP mode signal and the HS mode signal included in the MIPI D-PHY signal, corrects the attenuation of the HS mode signal (attenuation caused by cable transmission), multiplexes the separated LP mode signal and the HS mode signal subjected to the attenuation correction (returning to a signal format according to the MIPI D-PHY standard), and outputs the multiplexed signal to the processor 200. By doing so, the processor 200 can process the signal based on the MIPI D-PHY standard as it is without converting the signal into another format.

Furthermore, in the present embodiment, since the attenuation correction unit is provided in the scope connector 400 at a place other than the insertion portion of the endoscope device (scope) 100 and the endoscope operation unit (the attenuation correction unit is provided in the scope connector 400 in the embodiment, but the attenuation correction unit may be provided in other places, for example, a connector unit on the processor side or inside the processor 200), there is no need to increase the size of the insertion portion and the operation unit of the endoscope device.

<Specific Matters of Present Disclosure>

(1) Specific Matter 1

An endoscope system including:
an endoscope device that includes an endoscope-side connector unit;
a processor that includes a processor-side connector unit; and
an attenuation correction unit that corrects attenuation of a video signal from an image sensor disposed at a distal end portion of the endoscope device.

(2) Specific Matters 2

The endoscope system according to Specified Matter 1, in which the attenuation correction unit is provided in the endoscope-side connector unit.

(3) Specific Matter 3

The endoscope system according to Specified Matter 1 or 2, in which the video signal from the image sensor includes a signal conforming to an MIPI D-PHY standard, and
the attenuation correction unit includes:
a separation unit that separates the video signal into a low power mode signal and a high speed mode signal;
an equalizer unit that corrects attenuation of the high speed mode signal; and a driver signal processing unit that multiplexes the low power mode signal extracted from the video signal and the high speed mode signal subjected to the attenuation correction and outputs the multiplexed signal to the processor.

(4) Specific Matter 4

The endoscope system according to Specified Matter 3, in which the processor processes the video signal as a signal based on the MIPI D-PHY standard.

(5) Specific Matter 5

The endoscope system according to Specified Matter 3 or 4, in which the separation unit includes a first path for processing the low power mode signal and a second path for processing the high speed mode signal, a first type resistor and a comparator are provided in the first path, the first type resistor being connected in series with a signal line of the image sensor, the comparator being connected in series with the first type resistor and extracting a signal whose level is equal to or higher than a predetermined threshold level from signals passing through the first type resistor, and an equalizer that is connected in parallel with the signal line of the image sensor is provided in the second path.

(6) Specific Matter 6

The endoscope system according to Specified Matter 3 or 4, in which the separation unit includes a first path for processing the low power mode signal and a second path for processing the high speed mode signal, a comparator that is connected in series with a signal line of the image sensor and extracts a signal whose level is equal to or higher than a predetermined threshold level from the video signal is provided in the first path, and a switch and an equalizer are provided in the second path, the switch being connected in series with the signal line of the image sensor and being closed at a timing of extraction of the low power mode signal from the comparator, the equalizer being connected in parallel with the signal line of the image sensor.

(7) Specific Matter 7

The endoscope system according to Specified Matter 3 or 4, in which the separation unit includes a first path for processing the low power mode signal and a second path for processing the high speed mode signal, a first type switch and a comparator are provided in the first path, the first type switch being connected in series with a signal line of the image sensor, the comparator being connected in series with the signal line of the image sensor and extracting a signal whose level is equal to or higher than a predetermined threshold level from the video signal, a second type switch and an equalizer are provided in the second path, the second type switch being connected in series with the signal line of the image sensor, the equalizer being connected in parallel with the signal line of the image sensor, and the driver signal processing unit controls the first type switch to be turned on and controls the second type switch to be turned off so as to recognize, from the video signal input from the image sensor, a period of the low power mode signal and a period of the high speed mode signal, and, after recognizing the periods, the driver signal processing unit controls the first type switch to be turned on and controls the second type switch to be turned off during the period of the low power mode signal, and controls the first type switch to be turned off and controls the second type switch to be turned on during the period of the high speed mode signal.

(8) Specific Matter 8

The endoscope system according to Specified Matter 3 or 4, in which the separation unit includes a first path for processing the low power mode signal and a second path for processing the high speed mode signal, a transistor and a field effect transistor (FET) are provided in the first path, the transistor being connected in series with a signal line of the image sensor, the FET being connected in series with the signal line of the image sensor and extracting a signal whose level is equal to or higher than a predetermined threshold level from the video signal, a switch and an equalizer are provided in the second path, the switch being connected in series with the signal line of the image sensor, the equalizer being connected in parallel with the signal line of the image sensor, and the driver signal processing unit controls the switch to be turned off so as to recognize, from the video signal input from the image sensor, a period of the low power mode signal and a period of the high speed mode signal, and, after recognizing the periods, the driver signal processing unit controls the switch to be turned off during the period of the low power mode signal, and controls the switch to be turned on during the period of the high speed mode signal.

REFERENCE SIGNS LIST

1 Endoscope system
100 Endoscope device
110 Connector unit of endoscope device
200 Processor
210 Connector unit of processor
300 Monitor
400 Scope connector
401 Scope connector circuit
4011 Signal separation unit
4012 Equalizer unit
4013 Driver signal processing unit
4014 Control unit
4015 Memory

The invention claimed is:

1. An endoscope system comprising:
an endoscope device that includes an endoscope-side connector unit;
a processor that includes a processor-side connector unit; and
an attenuation correction unit that corrects attenuation of a video signal from an image sensor disposed at a distal end portion of the endoscope device.

2. The endoscope system according to claim 1, wherein the attenuation correction unit is provided in the endoscope-side connector unit.

3. The endoscope system according to claim 1, wherein the video signal from the image sensor includes a signal conforming to the MIPI D-PHY standard, and the attenuation correction unit includes:
a separation unit that separates the video signal into a low power mode signal and a high speed mode signal;
an equalizer unit that corrects attenuation of the high speed mode signal; and
a driver signal processing unit that multiplexes the low power mode signal extracted from the video signal and the high speed mode signal subjected to attenuation correction and outputs the multiplexed signal to the processor.

4. The endoscope system according to claim 3, wherein the processor processes the video signal as a signal based on the MIPI D-PHY standard.

5. The endoscope system according to claim 3, wherein the separation unit includes a first path for processing the low power mode signal and a second path for processing the high speed mode signal, a first type resistor and a comparator are provided in the first path, the first type resistor being connected in series with a signal line of the image sensor, the comparator being connected in series with the first type resistor and extracting a signal whose level is equal to or higher than a predetermined threshold level from signals passing through the first type resistor, and an equalizer that is connected in parallel with the signal line of the image sensor is provided in the second path.

6. The endoscope system according to claim 3, wherein the separation unit includes a first path for processing the low power mode signal and a second path for processing the high speed mode signal, a comparator that is connected in series with a signal line of the image sensor and extracts a signal whose level is equal to or higher than a predetermined threshold level from the video signal is provided in the first path, and a switch and an equalizer are provided in the second path, the switch being connected in series with the signal line of the image sensor and being closed at a timing of extraction of the low power mode signal from the comparator, the equalizer being connected in parallel with the signal line of the image sensor.

7. The endoscope system according to claim 3, wherein the separation unit includes a first path for processing the low power mode signal and a second path for processing the high speed mode signal, a first type switch and a comparator are provided in the first path, the first type switch being connected in series with a signal line of the image sensor, the comparator being connected in series with the signal line of the image sensor and extracting a signal whose level is equal to or higher than a predetermined threshold level from the video signal, a second type switch and an equalizer are provided in the second path, the second type switch being connected in series with the signal line of the image sensor, the equalizer being connected in parallel with the signal line of the image sensor, and the driver signal processing unit controls the first type switch to be turned on and controls the second type switch to be turned off so as to recognize, from the video signal input from the image sensor, a period of the low power mode signal and a period of the high speed mode signal, and, after recognizing the periods, the driver signal processing unit controls the first type switch to be turned on and controls the second type switch to be turned off during the period of the low power mode signal, and controls the first type switch to be turned off and controls the second type switch to be turned on during the period of the high speed mode signal.

8. The endoscope system according to claim 3, wherein the separation unit includes a first path for processing the low power mode signal and a second path for processing the high speed mode signal, a transistor and a field effect transistor (FET) are provided in the first path, the transistor being connected in series with a signal line of the image sensor, the FET being connected in series with the signal line of the image sensor and extracting a signal whose level is equal to or higher than a predetermined threshold level from the video signal, a switch and an equalizer are provided in the second path, the switch being connected in series with the signal line of the image sensor, the equalizer being connected in parallel with the signal line of the image sensor, and the driver signal processing unit controls the switch to be turned off so as to recognize, from the video signal input from the image sensor, a period of the low power mode signal and a period of the high speed mode signal, and, after recognizing the periods, the driver signal processing unit controls the switch to be turned off during the period of the low power mode signal, and controls the switch to be turned on during the period of the high speed mode signal.

* * * * *